US00PP20834P2

(12) United States Plant Patent
Bradford

(10) Patent No.: US PP20,834 P2
(45) Date of Patent: Mar. 16, 2010

(54) INTERSPECIFIC TREE NAME 'PLUMCANDY V'

(50) Latin Name: ***Prunus* sp.**
Varietal Denomination: Plumcandy V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,598

(22) Filed: Dec. 15, 2008

(51) Int. Cl.
*A01H 5/00* (2006.01)

(52) U.S. Cl. ..... Plt./180

(58) Field of Classification Search ..... Plt./180, Plt./184, 186
See application file for complete search history.

(56) References Cited

U.S. PATENT DOCUMENTS

PP15,809 P2 6/2005 Bradford

*Primary Examiner*—June Hwu

(57) ABSTRACT

The present invention relates to an interspecific tree and more particularly to a new and distinct variety broadly characterized by a large size, vigorous, hardy, and moderately productive tree. Being self-unfruitful, the present variety requires cross pollination from an apricot, interspecific, or plum that blooms during the early season. The fruit matures under the ecological conditions described during July, with first picking on Jul. 5, 2008. The fruit is uniformly small in size, mostly reddish brown skin color, clingstone in type, ovate to globose in shape, orange yellow in flesh color, firm in texture, and extremely sweet in flavor.

1 Drawing Sheet

Botanical classification: *Prunus* sp.
Varietal denomination: 'PLUMCANDY V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumcandy V'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing 'Yummygem' (U.S. Plant Pat. No. 15,809) plum was crossed by me in this manner. To pollinate this plum, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "10P881". They were grown as seedlings on their own root in my greenhouse and upon reaching dormancy transplanted to a cultivated area of my experimental orchard located near Le Grand, Calif. in Merced County (San Joaquin Valley). During the spring of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Yummygem' plum (U.S. Plant Pat. No. 15,809), by being a large tree, by blooming in the early season, by producing an abundance of pollen, and by producing fruit that is small in size, firm in texture, mostly red to reddish brown in skin color, and almost globose in shape, but is distinguished therefrom by producing fruit that is much sweeter with a hint of apricot flavor, that has apricot-like orange yellow flesh, and that matures about twenty-five days later.

The present variety is similar to Santa Rosa plum (unpatented) by producing fruit that matures near the first of July, that is fairly globose to ovate in shape, that is clingstone in type, and that has moderate freckling on the skin, but is distinguished therefrom by having a prolific bloom with abundant pollen and by producing fruit that is firmer, sweeter, less acidic toward both the skin and stone in taste, and orange yellow in flesh color instead of red and light yellow.

SUMMARY OF VARIETY

The present interspecific variety is characterized by a large size, vigorous, hardy, and moderately productive tree. Being self-unfruitful, the present variety requires cross pollination from an apricot, interspecific, or plum that blooms during the early season. The fruit matures under the ecological conditions described during July, with first picking on Jul. 5, 2008. The fruit is uniformly small in size, mostly reddish brown skin color, clingstone in type, ovate to globose in shape, orange yellow in flesh color, firm in texture, and extremely sweet in flavor.

DRAWING

The accompanying photograph consists of four whole fruits positioned to display the characteristics of the skin color and form, two half fruits sectioned to reveal the flesh and stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jul. 18, 2008, on the original tree during its seventh growing season. The flower and bud descriptions were developed during the previous blooming season. All major color code designations are by reference to the Inter-Society Color Council, National Bureau of Standards. Common color names are also used occasionally.

Parentage

Seed parent: 'Yummygem' plum (U.S. Plant Pat. No. 15,809).

Pollen parent: Unknown.

Tree

Size: Large, reaching a height of 12' [3.66 m.] and a spread of 12' [3.66 m.] after seven growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a vase form with rounded top.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium production, thinning usually necessary.

Fertility: Self-unfruitful, requiring cross pollination by a suitable early seasonal blooming apricot, interspecific, or plum, such as 'Blackred II' (U.S. Plant patent application Ser. No. 11/984,889 filed on Nov. 26, 2007).

Bearing: Regular bearer, with no crop failures observed.

Trunk:

- *Size.*—Medium, reaching a maximum diameter of 5½" [139.7 mm.] after the seventh growing season.
- *Texture.*—Medium shaggy.
- *Bark color.*—A Brownish gray [64. brGy] and Dark grayish yellowish brown [81. d.gy.yBr] variegation with Moderate orange yellow [71. m.OY] crevices present.
- *Lenticels.*—Approximate Number Per Square Inch: 10. Color: Brownish orange [54. br.O]. Average Size: ⅜" [9.5 mm.]. Shape: Elongated, eye-shaped.

Branches:

- *Size.*—Diameter of limb is 3½" [88.9 mm.] measured 12" above the crotch, 1⅞" [47.6 mm.] measured 12" above the first fork.
- *Texture.*—Smooth on first year wood, increasing roughness with age.
- *Color.*—1st Year Wood Topside: Moderate yellowish pink [29. m.yPk]. 1st Year Wood Underside: Brilliant yellow green [116. brill.YG]. 2$^{nd}$ Year Wood: Moderate brown [58. m.Br] with Light yellowish brown [76. l.yBr] crevices present.
- *Lenticels.*—Number Per Square Inch: More than 60 on second year wood. Color: Light grayish yellowish brown [79. l.gy.yBr]. Average Size: 1/32" [0.8 mm.]. Shape: Elongated, eye-shaped.

Leaves:

- *Size.*—Medium. Average Length: 4½" [114.3 mm.]. Average Width: 2" [50.8 mm.].
- *Arrangement.*—Alternate.
- *Thickness.*—Medium.
- *Form.*—Elliptical.
- *Apex.*—Acuminate.
- *Base.*—Acute with an average angle base angle of 75 degrees.
- *Surface.*—Smooth.
- *Color.*—Dorsal Surface: Moderate olive green [125. m.OlG]. Ventral Surface: Deep yellow green [118. deep YG].
- *Margin.*—Finely serrate.
- *Venation.*—Pinnately net veined.
- *Petiole.*—Average Length: ¼" [6.4 mm.]. Average Thickness: 1/16" [1.6 mm.]. Color: Moderate greenish yellow [102. m.gY] with some Moderate yellowish pink [29. m.yPk] areas where exposed to strong sunlight.
- *Stipules.*—Number: 2 per leaf in spring time, up to 6 per growing tip. Average Length: 5/16" [7.9 mm.]. Color: Very yellow green [115. v.YG] becoming Grayish reddish orange [39. gy.rO] with age.
- *Glands.*—Number: Mostly 2 to 3 per leaf. Position: Alternate and oppositely positioned near the intersection of the petiole and the base of the leaf blade. Size: Medium. Form: Globose. Color: Very yellow green [115. v.YG] acquiring Dark orange yellow [72. d.OY] centers with age. Leaf buds: Pointed, medium.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1⅛" [28.6 mm.],large than most.
- *Number of petals.*—Five, no double blossoms observed.
- *Petal shape.*—Oval to circular.
- *Petal margin.*—Entire, smooth to slightly wavy.
- *Average petal diameter.*—9/16" [14.3 mm.].
- *Average petal length.*—⅝" [15.9 mm.].
- *Petal apex.*—Rounded.

*Petal base.*—Obtuse.
*Petal color.*—White [263. White] on both sides.
*Anther color.*—Strong orange [50. s.O] over Brilliant yellow [83. brill.Y].
*Stigma color.*—Brilliant greenish yellow [98. brill.gY].
*Sepal color.*—Brilliant yellow green [116. brill.YG] on the outer surface, Light grayish red [18. l.gy.R] around the outer edges.
*Sepal length.*—5/32" [4.0 mm.].
*Sepal width.*—1/8" [3.2 mm.].
*Sepal apex.*—Rounded to elliptical to match the width and length.
*Sepal margin.*—Fairly smooth, with slight serrations toward the apex.
*Average pistil length.*—9/16" [14.3 mm.].
*Average stamen length.*—1/2" [12.7 mm.].
*Fragrance.*—Moderate.
*Pollen production.*—Abundant, extremely bee enticing.
*Bloom density.*—Moderate.
*Number per cluster.*—2 to 8, average 3.
*Blooming period.*—Early, with 'Ambra' plum (unpatented).
*Onset of bloom.*—One percent on Feb. 21, 2008.
*Date of full bloom.*—Feb. 28, 2008.
*Duration of bloom.*—One to two weeks, dependent on ambient temperature.

FRUIT

Maturity when described: Firm ripe, Jul. 18, 2008.
Date of first picking: Jul. 5, 2008.
Date of last picking: Jul. 25, 2008.
Size: Uniform, small.
*Average diameter axially.*—2 1/8" [54.0 mm.].
*Average diameter across cheek plane.*—2 7/16" [61.9 mm.].
*Average diameter across suture plane.*—2 1/4" [57.2 mm.].
*Typical weight.*—4.3 ounces [122 grams].
Form: Uniform, globose to somewhat ovate, symmetrical.
*Longitudinal section form.*—Oval.
*Transverse section through diameter.*—Round to elliptical.
Suture: A distinct Blackish red [21. blackish R] line located in a shallow trough extending from the base just to the pistol point.
Ventral surface: Rounded, lipped very slightly toward the base on both sides.
Lips: Equal.
Cavity: Flaring, rounded, suture showing on one side.
*Depth.*—7/16" [11.1 mm.].
*Breadth.*—1" [25.4 mm.].
Base: Truncate, slightly cordate if viewed parallel to the suture.
Apex: Mostly rounded.
Pistil point: An inconspicuous Dark orange yellow [72. d.OY] dot located at the end of the suture.
Stem: Longer than average.
*Average length.*—9/16" [14.3 mm.].
*Average width.*—3/32" [2.4 mm.].
Skin:
*Thickness.*—Medium.
*Surface.*—Smooth.
*Tenacity.*—Tenacious to the flesh.
*Astringency.*—Slight.
*Tendency to crack.*—Slight.
*Color.*—Deep reddish brown [44. d.rBr] over a Moderate yellow [87. m.Y] background with Dark orange yellow [72. d.OY] freckling throughout.
*Bloom.*—Abundant.
Flesh:
*Color.*—Brilliant orange yellow [67. brill.OY] from skin to stone, more typical of an apricot.
*Surface of pit cavity.*—Covered with Moderate orange yellow [71. m.OY] broken fibers when twisted away from stone.
*Amygdalin.*—Moderate.
*Juice.*—Abundant, very rich.
*Texture.*—Firm, Crisp.
*Fibers.*—Abundant, fine, tough.
*Ripens.*—Slightly earliest toward the apex.
*Flavor.*—An extremely sweet blend of acid and sugar with a hint of apricot, typically 26 to 30 brix.
*Aroma.*—Very slight.
*Eating quality.*—Outstanding.

STONE

Type: Clingstone.
Form: Oval.
Hilum: Narrow.
Base: Truncate.
Apex: Obtuse, with a sharp tip that is 3/32" [2.4 mm.] long.
Sides: Equal.
Surface: Rough throughout with furrows on each side of the dorsal fin.
External color of stone: Deep orange yellow [69. deep OY] with some Moderate yellowish brown [77. m.yBr] areas when first removed.
Pit wall color when cracked: Strong orange yellow [68. s.OY].
Cavity surface color: Light orange yellow [70. l.OY].
Average pit wall thickness: 1/16" [1.6 mm.]
Average width: 5/8" [15.9 mm.].
Average length: 7/8" [22.2 mm.].
Average breadth: 3/8" [9.5 mm.].
Tendency to split: Slight.
Kernel:
*Form.*—Oval.
*Skin color.*—Pale orange yellow [73. p.OY] when first removed.
*Pellicle color.*—Grayish yellowish brown [80. gy.yBr].
*Vein color.*—Light brown [57. l.Br].
*Taste.*—Slightly bitter.
*Viable.*—Yes.
*Average width.*—3/8" [9.5 mm.].
*Average length.*—1/2" [12.7 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'Yummygem' plum (U.S. Plant Pat. No. 15,809), by being a large tree, by blooming in the early season, by producing an abundance of pollen, and by producing fruit that is small in size, firm in texture, mostly red to reddish brown in skin color, and almost globose in shape, but is distinguished therefrom by producing fruit that is much sweeter with a hint of apricot flavor, that has apricot-like orange yellow flesh, and that matures about twenty-five days later.

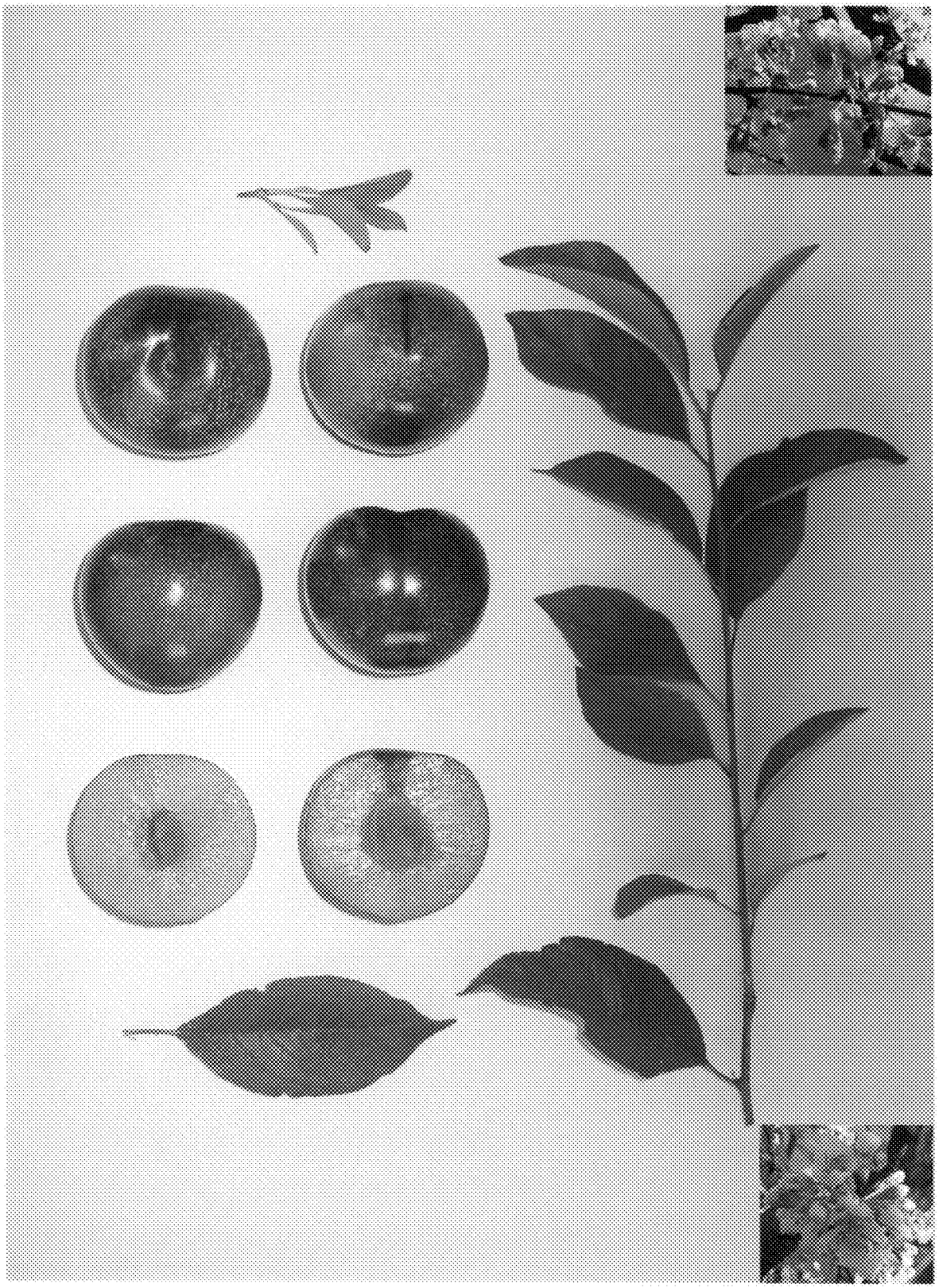

* * * * *